US012672807B2

(12) United States Patent
Burkholz et al.

(10) Patent No.: US 12,672,807 B2
(45) Date of Patent: Jul. 7, 2026

(54) BLOOD COLLECTION ADAPTER AND RELATED DEVICES TO REDUCE HEMOLYSIS

(71) Applicant: Becton, Dickinson and Company, Franklin Lakes, NJ (US)

(72) Inventors: Jonathan Karl Burkholz, Salt Lake City, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 267 days.

(21) Appl. No.: 17/146,388

(22) Filed: Jan. 11, 2021

(65) Prior Publication Data

US 2021/0228127 A1     Jul. 29, 2021

Related U.S. Application Data

(60) Provisional application No. 62/965,674, filed on Jan. 24, 2020.

(51) Int. Cl.
*A61B 5/15*         (2006.01)
*A61B 5/153*        (2006.01)

(52) U.S. Cl.
CPC .. *A61B 5/150992* (2013.01); *A61B 5/150366* (2013.01); *A61B 5/153* (2013.01)

(58) Field of Classification Search
CPC ........ A61B 5/150992; A61B 5/150366; A61B 5/153; A61B 5/150946; A61B 5/1535;

A61B 5/1545; A61B 5/15003; A61B 5/150732; A61B 5/154; A61B 5/150206; A61M 39/10; A61M 2039/1077
See application file for complete search history.

(56) References Cited

U.S. PATENT DOCUMENTS

| | | | |
|---|---|---|---|
| 4,492,634 A | | 1/1985 | Villa-Real |
| 5,531,672 A | * | 7/1996 | Lynn ................ A61B 5/150221 |
| | | | 604/38 |
| 7,662,110 B2 | | 2/2010 | Flaherty et al. |
| 10,682,474 B2 | | 6/2020 | Ring et al. |
| 2001/0031978 A1 | * | 10/2001 | Kipke ............. A61B 17/12022 |
| | | | 606/191 |
| 2003/0055381 A1 | | 3/2003 | Wilkinson |
| 2005/0027233 A1 | * | 2/2005 | Flaherty ........... A61B 5/150503 |
| | | | 600/576 |
| 2014/0042094 A1 | | 2/2014 | Montagu et al. |

(Continued)

FOREIGN PATENT DOCUMENTS

| | | |
|---|---|---|
| CN | 204016307 U | 12/2014 |
| EP | 1293162 A2 | 3/2003 |

(Continued)

*Primary Examiner* — Aurelie H Tu
(74) *Attorney, Agent, or Firm* — The Webb Law Firm

(57) ABSTRACT

An adapter may include a distal end, which may be configured to couple to a catheter assembly. The adapter may include a proximal end, which may include a proximal connector configured to couple to a blood collection device. The adapter may include a fluid pathway disposed between the distal end and the proximal end, wherein the fluid pathway includes a non-linear portion. The non-linear portion may form a coil shape, an S-shape, or another suitable shape.

20 Claims, 4 Drawing Sheets

(56) References Cited

U.S. PATENT DOCUMENTS

| | | | | |
|---|---|---|---|---|
| 2015/0025348 A1* | 1/2015 | Grabowski | ...... | A61B 5/150992 |
| | | | | 600/369 |
| 2015/0283334 A1* | 10/2015 | Marx | ................... | A61M 5/345 |
| | | | | 604/533 |
| 2016/0324455 A1 | 11/2016 | Crosby et al. | | |
| 2017/0120028 A1* | 5/2017 | Burkholz | .............. | A61M 39/10 |
| 2018/0140240 A1* | 5/2018 | Bullington | ....... | A61B 5/150396 |
| 2020/0050222 A1* | 2/2020 | Lane | ................. | G05D 16/0655 |

FOREIGN PATENT DOCUMENTS

| | | | |
|---|---|---|---|
| JP | 2007500540 A | 1/2007 | |
| JP | 2011055916 A | 3/2011 | |
| JP | 2015528328 A | 9/2015 | |
| JP | 2018167063 A | 11/2018 | |
| WO | 2013028759 A1 | 2/2013 | |

* cited by examiner

BLOOD COLLECTION ADAPTER AND RELATED DEVICES TO REDUCE HEMOLYSIS

RELATED APPLICATIONS

This application claims the benefit of U.S. Provisional Patent Application No. 62/965,674, filed Jan. 24, 2020, and entitled BLOOD COLLECTION ADAPTER AND RELATED DEVICES TO REDUCE HEMOLYSIS, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. A catheter assembly may include a catheter hub, the catheter extending distally from the catheter hub, and the introducer needle extending through the catheter. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

For blood withdrawal or collecting a blood sample from a patient, a blood collection container may be used. The blood collection container may include a syringe. Alternatively, the blood collection container may include a test tube with a rubber stopper at one end. In some instances, the test tube has had all or a portion of air removed from the test tube so pressure within the test tube is lower than ambient pressure. Such a blood collection container is often referred to as an internal vacuum or a vacuum tube. A commonly used blood collection container is a VACUTAINER® blood collection tube, available from Becton Dickinson & Company.

The blood collection container may be coupled to the catheter. When the blood collection container is coupled to the catheter, a pressure in the vein is higher than a pressure in the blood collection container, which pushes blood into the blood collection container, thus filling the blood collection container with blood. A vacuum within the blood collection container decreases as the blood collection container fills, until the pressure in the blood collection container equalizes with the pressure in the vein, and the flow of blood stops.

Unfortunately, as blood is drawn into the blood collection container, red blood cells are in a high shear stress state and susceptible to hemolysis due to a high initial pressure differential between the vein and the blood collection container. Hemolysis may result in rejection and discard of a blood sample. The high initial pressure differential can also result in catheter tip collapse, vein collapse, or other complications that prevent or restrict blood from filling the blood collection container. As the blood collection container fills, a pressure differential between the vein and the blood collection container decreases, and filling of the blood collection container with blood slows significantly.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to an adapter configured to reduce a likelihood of hemolysis during blood collection using a vascular access device, as well as related blood collection sets, systems, and methods. In some embodiments, the adapter may include a distal end, which may be configured to couple to a catheter assembly. In some embodiments, the adapter may include a proximal end, which may include a proximal connector configured to couple to a blood collection device. In some embodiments, the adapter may include a fluid pathway disposed between the distal end and the proximal end, wherein the fluid pathway includes a non-linear portion.

In some embodiments, the non-linear portion may form a coil shape, an S-shape, or another suitable shape. In some embodiments, the non-linear portion may extend through a tube. In some embodiments, the adapter may include a lumen, which may extend through the distal end of the adapter and the proximal end of the adapter. In some embodiments, the tube may be disposed within the lumen. In some embodiments, the adapter may include a middle portion disposed between the distal end and the proximal end. In some embodiments, the middle portion may surround the tube.

In some embodiments, the distal connector may include a male luer threaded connector, a male luer slip connector, a blunt cannula, or another suitable connector. In some embodiments, the proximal connector may include a female luer connector. In some embodiments, the proximal end may be coupled to a blood collection device. For example, the proximal end may be integrated with the blood collection device or monolithically formed with the blood collection device as a single unit. As another example, the proximal end may include the female luer connector, which may be coupled with a male luer connector of the blood collection device.

In some embodiments, the blood collection device may include a syringe. In some embodiments, the blood collection device may include a needle configured to pierce a seal of an evacuated blood collection tube. In these and other embodiments, the blood collection device may include a cylindrical holder, which may extend around the needle and may be configured to receive the evacuated blood collection tube.

It is to be understood that both the foregoing general description and the following detailed description are examples and explanatory and are not restrictive. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION

Figure 1A:
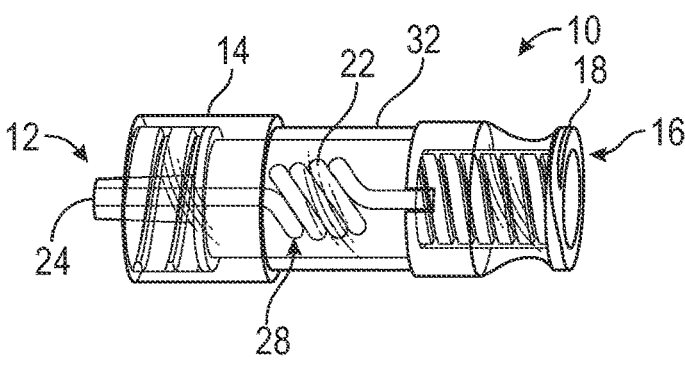
FIG. 1A is an upper perspective of an example adapter, according to some embodiments.
Figure 1B:
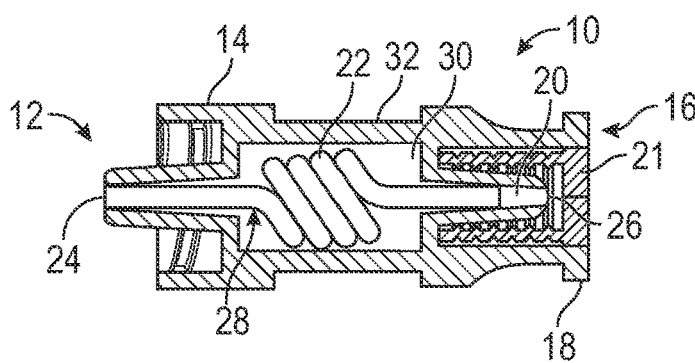
FIG. 1B is a cross-sectional view of the adapter of FIG. 1A, according to some embodiments.

Referring now to FIGS. 1A-1B, an adapter 10 is illustrated, according to some embodiments. In some embodiments, the adapter 10 may be configured to reduce a likelihood of hemolysis during blood collection using a vascular access device. In some embodiments, the vascular access device may include a catheter assembly. In some embodiments, the adapter 10 may include a distal end 12, which may include a distal connector 14 configured to couple to the catheter assembly. In some embodiments, the distal connector 14 may include a male luer threaded connector, as illustrated in FIGS. 1A-1B, or another suitable connector.

In some embodiments, the catheter assembly may include a catheter hub, which may include a distal end, a proximal end, and a lumen extending through the distal end and the proximal end. In some embodiments, the catheter assembly may include a catheter, which may be secured within the catheter hub and may extend distally from the distal end of the catheter hub. In some embodiments, the catheter may include a peripheral intravenous catheter (PIVC), a peripherally inserted central catheter (PICC), or a midline catheter.

In some embodiments, the catheter assembly may include or correspond to any suitable catheter assembly. In some embodiments, the catheter assembly may be integrated and include an extension tube, which may extend from and be integrated with a side port of the catheter hub. A non-limiting example of an integrated catheter assembly is the BD NEXIVA™ Closed IV Catheter system, available from Becton Dickinson and Company of Franklin Lakes, New Jersey. In some embodiments, a proximal end of the extension tube may be coupled to another adapter, such as, for example, a Y-adapter. In some embodiments, the adapter 10 may be configured to couple to the other adapter.

In some embodiments, the catheter assembly may be non-integrated and may not include the extension tube. In these and other embodiments, the adapter 10 may be configured to couple to the proximal end of the catheter hub or another suitable portion of the catheter assembly. In some embodiments, the adapter 10 may be coupled directly to the catheter adapter, eliminating the extension tube and providing a compact catheter system.

In some embodiments, the adapter 10 may include a proximal end 16, which may include a proximal connector 18 configured to couple to a blood collection device. In some embodiments, the proximal connector 18 may include a female luer connector or another suitable connector. In some embodiments, the adapter 10 may include a fluid pathway 20 disposed between the distal end 12 and the proximal end 16. In some embodiments, fluid within the fluid pathway 20 may flow through the distal end 12 and/or the proximal end 16. In some embodiments, the fluid within the fluid pathway 20 may flow through the proximal end 16 in response to opening of a septum 21 disposed within the proximal end 16. In some embodiments, the septum 21 may open in response to coupling of the blood collection device to the proximal end 16 of the adapter 10. In some embodiments, the septum 21 may include any suitable septum and may be different from the septum 21 illustrated. In some embodiments, the septum 21 may include an accordion-like septum 21 that may open when compressed in a distal direction.

In some embodiments, the fluid pathway 20 may include a non-linear portion 22. Blood cells may experience shear stress as they flow through the fluid pathway 20. The maximum shear stress is along the wall of the blood cell, or wall shear stress. Wall shear stress on blood cells is considered a major source of mechanical damage to blood cells. In some embodiments, the non-linear portion may facilitate increased flow resistance within the vascular access system to distribute the pressure differential and reduce shear stress experienced by red blood cells.

In some embodiments, the non-linear portion 22 may form a coil shape, an S-shape, or another suitable shape. As illustrated in FIGS. 1A-1B, in some embodiments, the non-linear portion 22 may include the coil shape, which may include a spiral. In some embodiments, no fluid flowing through the non-linear portion may flow in a straight line. In some embodiments, the non-linear portion 22 may increase a length of the fluid pathway 20 through the adapter 10 and thereby may increase flow resistance and decrease blood flow within the adapter 10. In these embodiments, a risk of hemolysis during blood collection may be reduced.

In some embodiments, a length of the fluid pathway 20 of the adapter 10 may be selected based on one or more of the following: a gauge and/or length of the catheter, a configuration of the catheter assembly configuration, or a clinical setup. In some embodiments, the fluid pathway 20 may include a length L. In some embodiments, the length L may extend from a distal end of the fluid pathway 20 to a proximal end of the fluid pathway 20. As an example, the length L may extend from a distal end 24 of the fluid pathway 20 to a proximal end 26 of the fluid pathway 20. As another example, the length L may extend from a distal end of a tube 28 to a proximal end of the tube 28. In some embodiments, the length L may correspond to a length or an entire length of the adapter 10. In some embodiments, the fluid pathway 20 may extend along the entire length of the adapter 10 from a distal-most portion of the adapter 10 to a proximal-most portion of the adapter 10. In some embodiments, the fluid pathway 20 may include an inner diameter D. In some embodiments, the inner diameter D may be constant along the length L.

Fluid flow in the fluid pathway 20, which may be tubular, can be analyzed using Poiseuille's equation:

$$Q = \frac{\pi D^4 \Delta P}{128 \mu L} = \frac{\Delta P}{R_f}$$

where $\Delta P$ is a change in pressure gradient across the length of the fluid pathway 20, D and L are the inner diameter and length, respectively, of the fluid pathway 20, $\mu$ is the viscosity of a fluid, and $$R_f = \frac{128 \mu L}{\pi D^4}$$

is the fluid resistance. Since $\mu$ is the viscosity of the fluid and not part of the extension tube geometry, a geometric factor $G_f$ is defined such that $R_f$ (the fluid resistance) is $$R_f = \frac{128 \mu}{\pi} G_f, \text{ where } G_f = \frac{L}{D^4}.$$

In some embodiments, the fluid pathway 20 may have multiple sections with lengths (L1, L2, L3) and inner diameters of (D1, D2, D3), the geometric factor is then:

$$G_f = \frac{L1}{D1^4} + \frac{L2}{D2^4} + \frac{L3}{D3^4}$$

In some embodiments, the fluid pathway 20 may have an inner diameter that changes over the length of the fluid pathway 20, the geometric factor is then:

$$G_f = \int_0^L \frac{dl}{D(l)^4}$$

In some embodiments, the fluid pathway 20 may have a cross section that is not circular or may have a complicated inner diameter profile. The geometric factor can then be determined by measuring the flow rate (Q) at given pressure ($\Delta P$) with known viscosity ($\mu$) fluid:

$$G_f = \frac{\pi \Delta P}{128 \mu Q}$$

The $G_f$ value of the fluid pathway 20 may be selected to reduce the maximum shear stress for each catheter gauge to be the same or less than the maximum shear stress of a BD 21 G VACUTAINER® UltraTouch™ push button blood collection set (available from Becton, Dickinson & Company of Franklin Lakes, New Jersey), which was previously considered the gold standard for blood draws. In some embodiments, $G_f$ may be equal to or more than 3.83E+06 (1/in³) when a 18 G catheter is used, which may reduce the wall sheer stress to reduce hemolysis. In some embodiments, $G_f$ may be equal to or more than 3.27E+06 (1/in³) when a 20 G catheter is used, which may reduce the wall sheer stress to reduce hemolysis. In some embodiments, $G_f$ may be equal to or more than 3.33E+06 (1/in³) when a 22 G catheter is used, which may reduce the wall sheer stress to reduce hemolysis. In some embodiments, $G_f$ may be equal to or more than 1.50E+07 (1/in³) when a 24 G catheter is used, which may reduce the wall sheer stress to reduce hemolysis. In some embodiments, $G_f$ may include another value. In some embodiments, $G_f$ value of the fluid pathway may be selected to reduce the maximum shear stress for each catheter gauge to be the same or less than the maximum shear stress of a BD 25 G VACUTAINER® UltraTouch™ push button blood collection set (available from Becton, Dickinson & Company of Franklin Lakes, New Jersey).

In some embodiments, when a 18 G catheter is used, $G_f$ may be equal to 3.83E+06 (1/in³) plus or minus 10 percent, plus or minus 25 percent, plus or minus 50 percent, or plus or minus 75 percent, which may reduce the wall sheer stress to reduce hemolysis. In some embodiments, when a 20 G catheter is used, $G_f$ may be equal to 3.27E+06 (1/in³) plus or minus 10 percent, plus or minus 25 percent, plus or minus 50 percent, or plus or minus 75 percent, which may reduce the wall sheer stress to reduce hemolysis. In some embodiments, when a 22 G catheter is used, $G_f$ may be equal to 3.33E+06 (1/in³) plus or minus 10 percent, plus or minus 25 percent, plus or minus 50 percent, or plus or minus 75 percent, which may reduce the wall sheer stress to reduce hemolysis. In some embodiments, when a 24 G catheter is used, $G_f$ may be equal to 1.50E+07 (1/in³) plus or minus 10 percent, plus or minus 25 percent, plus or minus 50 percent, or plus or minus 75 percent, which may reduce the wall sheer stress to reduce hemolysis. In some embodiments, $G_f$ may include another value, which may be selected based on a gauge of the catheter. In some embodiments, $G_f$ values may be selected to be the same for 22 G through 18 G catheters.

In some embodiments, the non-linear portion 22 may reduce the risk of hemolysis, while at the same time facilitating a compact adapter 10. In some embodiments, the non-linear portion 22 may extend through the tube 28, the groove 56 (see, for example, FIGS. 6A-6C) or another suitable structure. In some embodiments, a distal end of the tube 28 and/or a proximal end of the tube 28 may be secured within the adapter 10 at various suitable locations.

In some embodiments, the adapter 10 may include a lumen 30, which may extend through the distal end 12 of the adapter 10 and the proximal end 16 of the adapter 10. In some embodiments, the tube 28 may be disposed within the lumen 30. In some embodiments, the adapter 10 may include a middle portion 32 disposed between the distal end 12 and the proximal end 16. In some embodiments, the middle portion 32 may surround the tube 28. In some embodiments, the adapter 10 may house the tube 28 with the only openings in the adapter 10 being at the distal end 12 and the proximal end 16.

Referring now to FIGS. 2A-2D, in some embodiments, the proximal end 16 may be coupled to the blood collection device 34. For example, the proximal end 16 may be integrated with the blood collection device 34 or monolithically formed with the blood collection device 34 as a single unit. As another example, the proximal end 16 may include the female luer connector, which may be coupled with a male luer connector of the blood collection device 34.

Figure 2A:
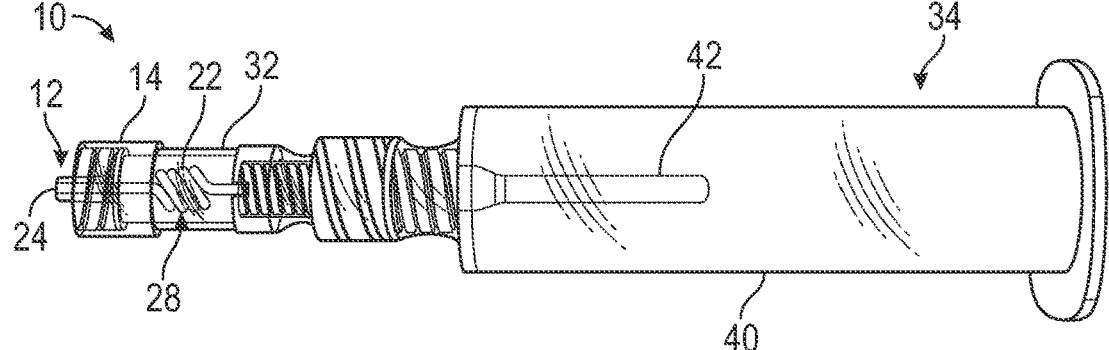
FIG. 2A is an upper perspective view of the adapter of FIG. 1A integrated with an example blood collection device, according to some embodiments.
Figure 2B:
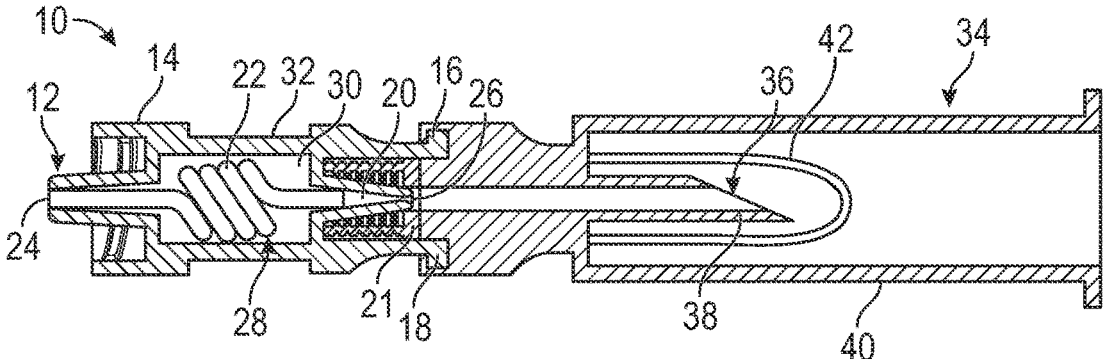
FIG. 2B is a cross-sectional view of the adapter of FIG. 1A integrated with the blood collection device of FIG. 2A, according to some embodiments.

As illustrated in FIG. 2A, in some embodiments, the blood collection device 34 may include a needle assembly 36, which may include a needle 38 configured to receive a blood collection container. In these and other embodiments, the blood collection container may include an evacuated blood collection tube. In some embodiments, the blood collection container may have all or a portion of air removed so pressure within the blood collection container is lower than ambient pressure.

In some embodiments, the needle assembly 36 may include one or more threads, which may be configured to couple to a holder 40, which may be generally cylindrical and may be configured to hold the blood collection container. In some embodiments, the holder 40 may be integrally formed with the needle assembly 36 or coupled to the needle assembly 36 via bonding or another suitable method. In some embodiments, the holder 40 may surround the needle 38. In some embodiments, the needle assembly 36 and the holder 40 may include or correspond to a luer lock access device, such as, for example, the VACUTAINER® LUER-LOK™ Access Device available from Becton, Dickinson and Company of Franklin Lakes, New Jersey. In some embodiments, a distal end of the needle assembly 36 may include the male luer connector compatible with the proximal connector 18.

In some embodiments, a proximal end of the needle 38 may be enveloped within an elastomeric sheath 42. In some embodiments, the elastomeric sheath 42 may include an open distal end and a closed proximal end. In some embodiments, in response to the blood collection container 34 pushing the elastomeric sheath 26 distally, the needle 38 may pierce the elastomeric sheath 42, and the needle 38 may insert into a cavity of the blood collection container.

In some embodiments, the fluid pathway of the vascular access system, which may include one or more of the needle assembly 36, the adapter 10, and the catheter assembly 37 (which may include an extension tube), may include an entirety of a blood collection pathway through which blood flows during blood collection. The system geometric factor $G_{fs}$ for the fluid pathway of the vascular access system can be determined in similar fashion as described earlier. In some embodiments, the system geometric factor $G_{fs}$ may be equal to or more than 7.34E+06 (1/in$^3$). In some embodiments, $G_{fs}$ may include another value. In some embodiments, the system geometric factor $G_{fs}$ may be 7.34E+06 (1/in$^3$) plus or minus 10 percent, plus or minus 25 percent, plus or minus 50 percent, or plus or minus 75 percent. In some embodiments, $G_{fs}$ may include another value, which may be selected based on a gauge and/or length of the catheter. In some embodiments, an inner diameter of the adapter 10 may be equal to or greater than a smallest inside diameter of a rest of the complete blood collection pathway for blood collection.

Figure 2C:
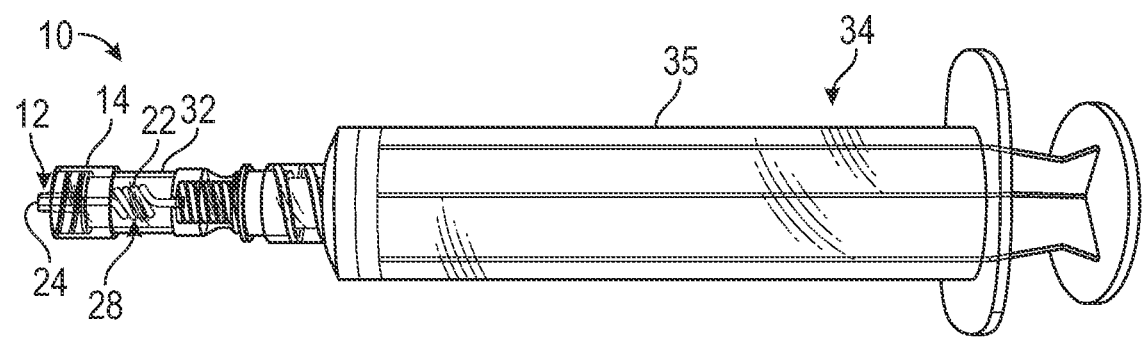
FIG. 2C is an upper perspective view of the adapter of FIG. 1A integrated with another example blood collection device, according to some embodiments.

As illustrated in FIG. 2C, in some embodiments, the blood collection device 34 may include a syringe 35, which may include a depressible plunger.

Figure 2D:
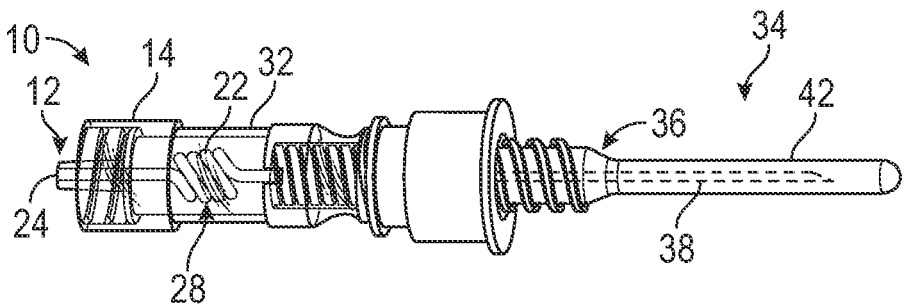
FIG. 2D is an upper perspective view of the adapter of FIG. 1A integrated with another example blood collection device, according to some embodiments.

As illustrated in FIG. 2D, in some embodiments, the blood collection device 34 may include the needle assembly 36, which may not include the holder 40.

Figure 3A:
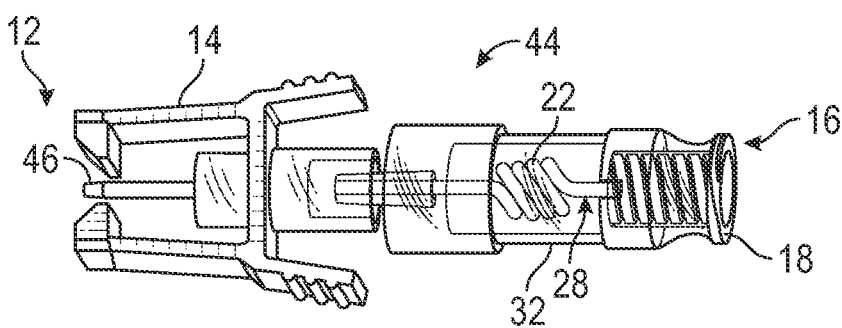
FIG. 3A is an upper perspective view of another example adapter, according to some embodiments.
Figure 3B:
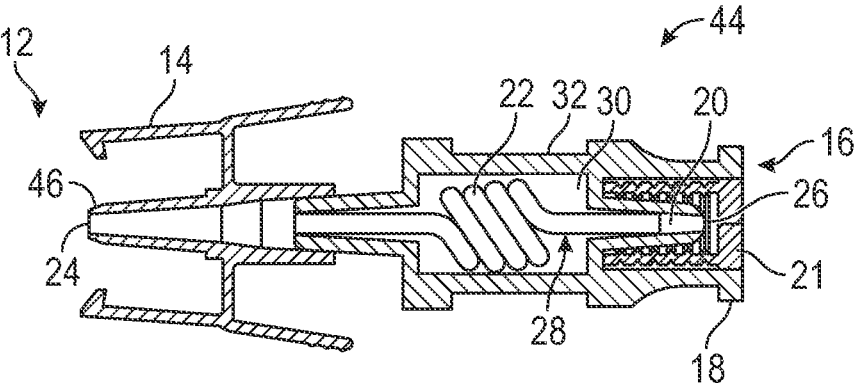
FIG. 3B is a cross-sectional view of the adapter of FIG. 3A, according to some embodiments.

Referring now to FIGS. 3A-3B, an adapter 44 is illustrated, according to some embodiments. In some embodiments, the adapter 44 may be similar or identical to the adapter 10 of FIGS. 1A-2D in terms of one or more included features and/or operation. In some embodiments, the distal connector 14 of the adapter 10 may include a blunt cannula 46 which may insert into a portion of the catheter assembly and/or one or more arms 48 that may clip onto a portion of the catheter assembly.

Figure 4A:
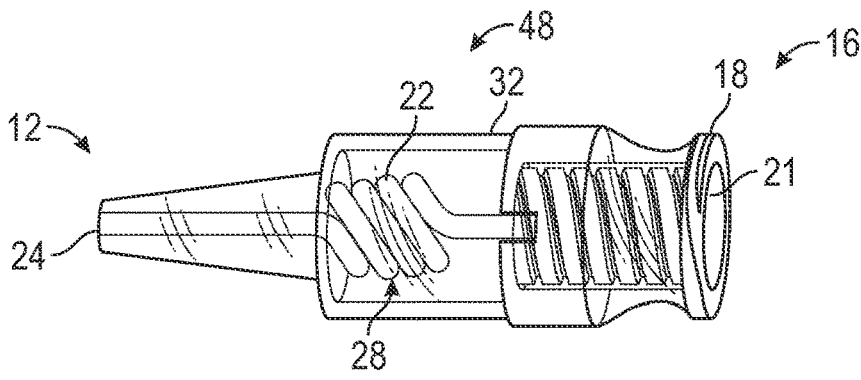
FIG. 4A is an upper perspective view of another example adapter, according to some embodiments.
Figure 4B:
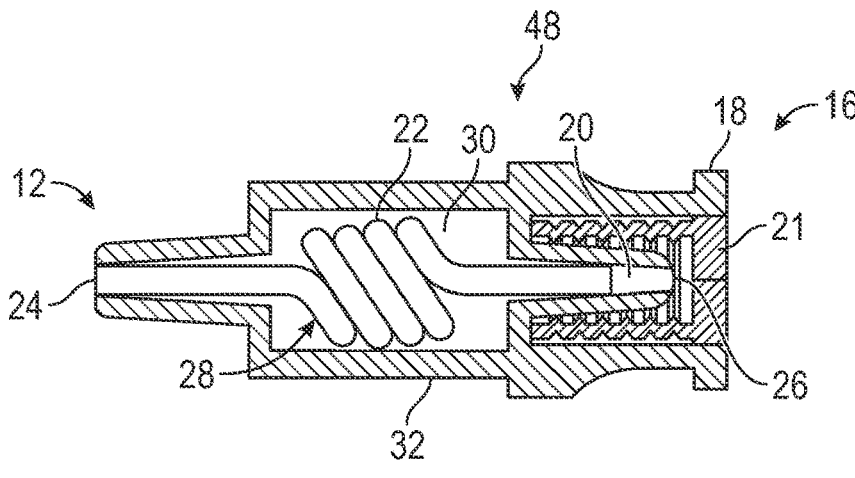
FIG. 4B is a cross-sectional view of the adapter of FIG. 4A, according to some embodiments.

Referring now to FIGS. 4A-4B, an adapter 48 is illustrated, according to some embodiments. In some embodiments, the adapter 48 may be similar or identical to the adapter 10 of FIGS. 1A-2D and/or the adapter 44 of FIGS. 3A-3B in terms of one or more included features and/or operation. In some embodiments, the distal connector 14 of the adapter 10 may include a male luer slip connector 50.

Figure 5:
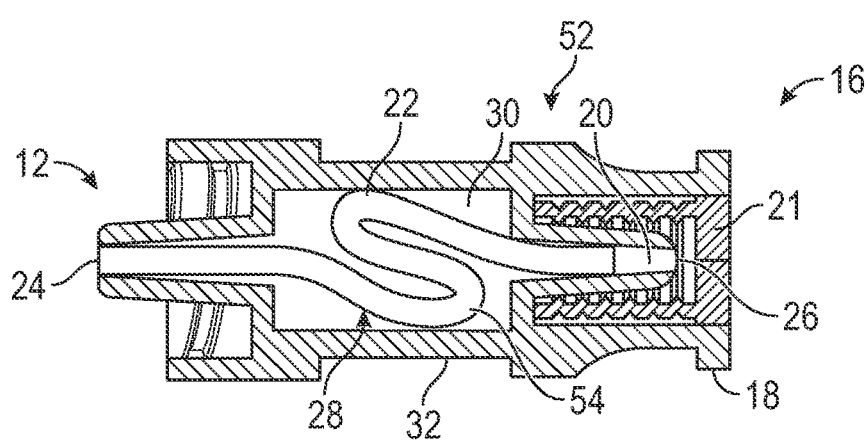
FIG. 5 is a cross-sectional view of another example adapter, according to some embodiments.

Referring now to FIG. 5, an adapter 52 is illustrated, according to some embodiments. In some embodiments, the adapter 52 may be similar or identical in terms of one or more included features and/or operation to one or more of the following: the adapter 10 of FIGS. 1A-2D, the adapter 44 of FIGS. 3A-3B, and the adapter 48 of FIGS. 4A-4B. In some embodiments, the non-linear portion 22 may form an S-shape 54 or another suitable shape.

Figure 6A:
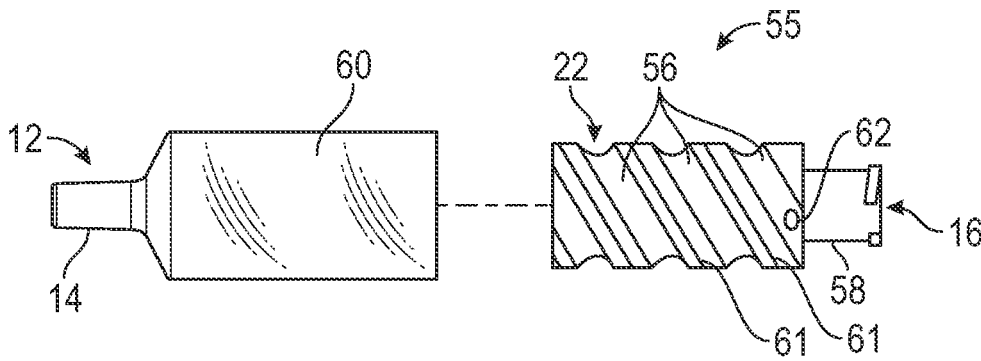
FIG. 6A is an exploded view of another example adapter, according to some embodiments.
Figure 6B:
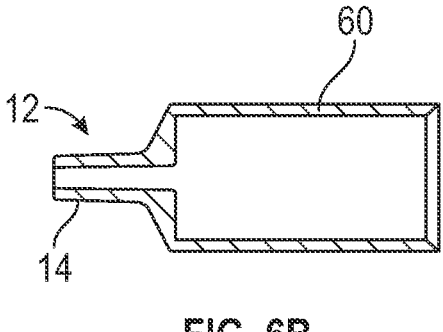
FIG. 6B is a cross-sectional view of an example outer component, according to some embodiments.
Figure 6C:
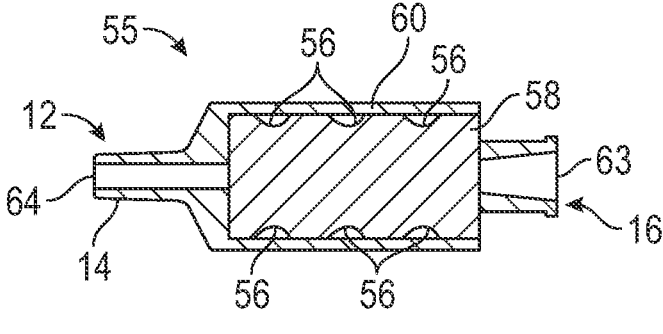
FIG. 6C is a cross-sectional view of the adapter of FIG. 6A, according to some embodiments.

Referring now to FIGS. 6A-6C, an adapter 55 is illustrated, according to some embodiments. In some embodiments, the adapter 55 may be similar or identical in terms of one or more included features and/or operation to one or more of the following: the adapter 10 of FIGS. 1A-2D, the adapter 44 of FIGS. 3A-3B, the adapter 48 of FIGS. 4A-4B, and the adapter 52 of FIG. 5. For example, the adapter 55 may be coupled to the blood collection device 34 (see, for example, FIGS. 2A-2D).

In some embodiments, the non-linear portion 22 of the fluid pathway 20 may include a channel or a groove 56. In some embodiments, the groove 56 may be disposed in an outer surface of an inner component 58, which may be coupled to an outer component 60. In some embodiments, the groove 56 may include a coil or spiral shape. In some embodiments, the groove 56 may be proximate an inner surface of the outer component 60, which may close the groove 56 such that fluid flowing through the groove 56 may not escape the groove 56 except at a distal end and a proximal end of the groove 56.

In some embodiments, contact between the inner component 58 and the outer component 60 may form a seal between the inner component 58 and the outer component 60. In some embodiments, the outer surface of the inner component 58 may include a seal element 61, which may include silicon, rubber, plastic, or another suitable material. In some embodiments, the seal element 61 may include a coil or spiral shape and may be offset from the groove 56 in the distal-proximal direction. In some embodiments, the seal element 61 may prevent fluid from escaping the groove 56 except at a distal end and a proximal end of the groove 56.

In some embodiments, an outer diameter of the inner component 58 may be approximately equal to or slightly less than an inner diameter of the outer component 60 such that the inner component 58 is fitted within the outer component 60. In some embodiments, the inner surface of the outer component 60 may be generally cylindrical, and the outer surface of the inner component 58 may be generally cylindrical. In some embodiments, the inner component 58 and the outer component 60 may be concentric. In some embodiments, the inner component 58 and the outer component 60 may be integrally formed or monolithically formed as a single unit.

In some embodiments, the outer component 60 may include the distal end 12, which may include the distal connector 14 of FIG. 1, 3, or 4 or another suitable connector. In some embodiments, the inner component 58 may include the proximal end 16, which may include the proximal connector 18 such as a female luer connector or another suitable connector.

In some embodiments, a proximal end of the groove 56 may include a hole 62 that may fluidically connect the groove 56 to an opening 63 of the proximal end 16. Similarly, in some embodiments, a distal end of the groove 56 may include a hole that may fluidically connect the groove 56 to an opening 64 of the distal end 12.

All examples and conditional language recited herein are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

We claim:

1. An adapter, comprising:
a distal end, comprising a distal connector configured to couple to a catheter assembly;
a proximal end, comprising a proximal connector configured to couple to a blood collection device;
a middle portion disposed between the distal end and the proximal end and joining the distal connector to the proximal connector, the middle portion being integrally formed with the distal connector and the proximal connector to provide a singular, unitary adapter body, with a lumen extending through the distal end, the middle portion, and the proximal end; and
a tube positioned within the lumen, in the middle portion, the tube defining a fluid pathway disposed between the distal end and the proximal end, wherein the fluid pathway includes a non-linear portion;
wherein each of the proximal connector and the distal connector comprises a luer connector integrally formed with the middle portion, with the distal luer connector extending out distally from the middle portion to form the distal end and the proximal luer connector extending out proximally from the middle portion to form the proximal end; and
wherein the fluid pathway comprises a geometric factor, $G_f$, configured to reduce hemolysis in blood flowing proximally through the adapter to the blood collection device.

2. The adapter of claim 1, wherein the non-linear portion forms a coil shape.

3. The adapter of claim 1, wherein the non-linear portion forms an S-shape.

4. The adapter of claim 1, wherein the distal connector comprises a male luer threaded connector including a collar positioned about a male extension member.

5. The adapter of claim 1, wherein the distal connector comprises a male luer slip connector including a male extension member.

6. The adapter of claim 1, wherein the distal connector further comprises a blunt cannula extending out distally from the luer connector at the distal end.

7. The adapter of claim 1, wherein the proximal connector comprises a female luer connector including a cavity configured to receive a male luer connector.

8. The blood collection set of claim 1, wherein the geometric factor, $G_f$, is defined as:

$$G_f = L/D^4$$

where L is a length of the fluid pathway and D is a diameter of the fluid pathway.

9. The blood collection set of claim 8, wherein the geometric factor, $G_f$, is one of:
3.83E+06 ($1/in^3$) plus or minus 10 percent, plus or minus 25 percent, plus or minus 50 percent, or plus or minus 75 percent;
3.27E+06 ($1/in^3$) plus or minus 10 percent, plus or minus 25 percent, plus or minus 50 percent, or plus or minus 75 percent;
3.33E+06 ($1/in^3$) plus or minus 10 percent, plus or minus 25 percent, plus or minus 50 percent, or plus or minus 75 percent; or
1.50E+07 ($1/in^3$) plus or minus 10 percent, plus or minus 25 percent, plus or minus 50 percent, or plus or minus 75 percent.

10. A blood collection set, comprising:
a blood collection device; and
an adapter, comprising:
a distal end, comprising a distal connector configured to couple to a catheter assembly;
a proximal end, comprising a proximal connector coupled to the blood collection device;
a middle portion disposed between the distal end and the proximal end and joining the distal connector to the proximal connector, the middle portion being integrally formed with the distal connector and the proximal connector to provide a singular, unitary adapter body, with a lumen extending through the distal end, the middle portion, and the proximal end; and
a tube positioned within the lumen, in the middle portion, the tube defining a fluid pathway disposed between the distal end and the proximal end, wherein the fluid pathway includes a non-linear portion;
wherein each of the proximal connector and the distal connector comprises a luer connector integrally formed with the middle portion, with the distal luer connector extending out distally from the middle portion to form the distal end and the proximal luer connector extending out proximally from the middle portion to form the proximal end; and
wherein the tube and the fluid pathway defined thereby is configured to reduce hemolysis in blood flowing proximally through the adapter to the blood collection device.

11. The blood collection set of claim 10, wherein the blood collection device comprises a syringe.

12. The blood collection set of claim 10, wherein the blood collection device comprises a needle configured to pierce a seal of an evacuated blood collection tube.

13. The blood collection set of claim 12, wherein the blood collection device further comprises a cylindrical holder extending around the needle.

14. The blood collection set of claim 10, wherein the non-linear portion forms a coil shape.

15. The blood collection set of claim 10, wherein the non-linear portion forms an S-shape.

16. The blood collection set of claim 10, wherein the distal connector comprises one of a male luer threaded connector, a male luer slip connector, and a blunt cannula.

17. The blood collection set of claim 10, wherein the proximal connector comprises a female luer connector.

18. The blood collection set of claim 10, wherein the fluid pathway comprises a geometric factor, Gr, configured to reduce hemolysis in blood flowing through the adapter to the blood collection device, the geometric factor defined as:

$$G_f = L/D^4$$

where L is a length of the fluid pathway and D is a diameter of the fluid pathway.

19. The blood collection set of claim 18, wherein the geometric factor, $G_f$, is one of:

3.83E+06 (1/in$^3$) plus or minus 10 percent, plus or minus 25 percent, plus or minus 50 percent, or plus or minus 75 percent;

3.27E+06 (1/in$^3$) plus or minus 10 percent, plus or minus 25 percent, plus or minus 50 percent, or plus or minus 75 percent;

3.33E+06 (1/in$^3$) plus or minus 10 percent, plus or minus 25 percent, plus or minus 50 percent, or plus or minus 75 percent; or 1.50E+07 (1/in$^3$) plus or minus 10 percent, plus or minus 25 percent, plus or minus 50 percent, or plus or minus 75 percent.

20. A method for collecting a blood sample comprising: providing an adapter, comprising:

a distal end, comprising a distal connector configured to couple to a catheter assembly;

a proximal end, comprising a proximal connector;

a middle portion disposed between the distal end and the proximal end and joining the distal connector to the proximal connector, the middle portion being integrally formed with the distal connector and the proximal connector to provide a singular, unitary adapter body, with a lumen extending through the distal end, the middle portion, and the proximal end; and a tube positioned within the lumen, in the middle portion, the tube defining a fluid pathway disposed between the distal end and the proximal end, wherein the fluid pathway includes a non-linear portion;

wherein each of the proximal connector and the distal connector comprises a luer connector integrally formed with the middle portion, with the distal luer connector extending out distally from the middle portion to form the distal end and the proximal luer connector extending out proximally from the middle portion to form the proximal end;

coupling the distal connector to the catheter assembly to place the catheter assembly in fluid communication with the adapter;

coupling the proximal connector to a blood collection device to place the blood collection device in fluid communication with the adapter; and collecting a blood sample in the blood collection device, to enable further testing of the blood sample, with the blood sample flowing through the catheter assembly and the adapter and into the blood collection device, with blood flowing through an entirety of the non-linear portion as the blood travels through the adapter.

\* \* \* \* \*